United States Patent
Beume et al.

(10) Patent No.: US 8,648,100 B2
(45) Date of Patent: Feb. 11, 2014

(54) ROFLUMILAST FOR THE TREATMENT OF PULMONARY HYPERTENSION

(75) Inventors: Rolf Beume, Constance (DE); Armin Hatzelmann, Constance (DE); Degenhard Marx, Moos (DE); Christian Schudt, Constance (DE); Hermann Tenor, Radolfzell (DE); Saadia Eddahibi, Paris (FR); Serge Adnot, Saint Maur des Fossés (FR)

(73) Assignee: Takeda GmbH, Konstanz (DE)

( * ) Notice: Subject to any disclaimer, the term of this patent is extended or adjusted under 35 U.S.C. 154(b) by 1272 days.

(21) Appl. No.: 11/918,397

(22) PCT Filed: Apr. 12, 2006

(86) PCT No.: PCT/EP2006/061557
§ 371 (c)(1),
(2), (4) Date: Jan. 16, 2008

(87) PCT Pub. No.: WO2006/111495
PCT Pub. Date: Oct. 26, 2006

(65) Prior Publication Data
US 2009/0215836 A1    Aug. 27, 2009

(30) Foreign Application Priority Data
Apr. 19, 2005  (EP) .................................. 05103147

(51) Int. Cl.
*A61K 31/44* (2006.01)
*C07D 213/74* (2006.01)

(52) U.S. Cl.
USPC ........................................... 514/352; 546/309

(58) Field of Classification Search
None
See application file for complete search history.

(56) References Cited

U.S. PATENT DOCUMENTS

| | | | |
|---|---|---|---|
| 5,712,298 A | 1/1998 | Amschler | |
| 6,239,130 B1 | 5/2001 | Pascal et al. | |
| 6,331,543 B1 | 12/2001 | Garvey et al. | |
| 6,333,354 B1 * | 12/2001 | Schudt ........................... | 514/573 |
| 2003/0023087 A1 | 1/2003 | Garvey et al. | |
| 2003/0186974 A1 | 10/2003 | Marfat et al. | |
| 2004/0087591 A1 | 5/2004 | Garvey et al. | |
| 2004/0261190 A1 | 12/2004 | Eggenweiler et al. | |
| 2005/0020626 A1 | 1/2005 | Mathias | |
| 2005/0020639 A1 | 1/2005 | Smith et al. | |
| 2005/0043326 A1 | 2/2005 | Barber et al. | |
| 2005/0049258 A1 | 3/2005 | Marfat et al. | |

FOREIGN PATENT DOCUMENTS

| | | | |
|---|---|---|---|
| WO | 95/01338 A1 | 1/1995 | |
| WO | 95/09636 A1 | 4/1995 | |
| WO | 98/37894 A1 | 9/1998 | |
| WO | 03/070279 A1 | 8/2003 | |
| WO | 2004/096274 A1 | 11/2004 | |
| WO | 2004/103407 A2 | 12/2004 | |
| WO | 2004/105751 A1 | 12/2004 | |
| WO | 2005/018624 A2 | 3/2005 | |
| WO | 2005/102317 A1 | 11/2005 | |

OTHER PUBLICATIONS

Nazzareno Galié, "Guidelines on diagnosis and treatment of pulmonary arterial hypertension." European Heart Journal, v.25, pp. 2243-2278 (2004).
Ghofrani et al., "Sildenafil for treatment of lung fibrosis and pulmonary hypertension: a randomised controlled trial." The Lancet, v.360:9337, pp. 895-900 (2002).
Mealy and Bayés, "Annual Update 2004/2005—Treatment of Respiratory Disorders." Drugs of the Future, v.30:1, pp. 51-112 (2005).
Phillips et al., "cAMP phosphodiesterase inhibitors potentiate effects of prostacyclin analogs in hypoxic pulmonary vascular remodeling." Am. J. Physiol. Lung Cell. Mol. Physiol., v.288, pp. 103-115 (2004).
Peter Reid, "Roflumilast—Altana Pharma." Current Opinion in Investigational Drugs, v.3:8, pp. 1165-1170 (2002).
Schermuly et al., "Antiremodeling Effects of Iloprost and the Dual-Selective Phosphodiesterase 3/4 Inhibitor Tolafentrine in Chronic Experimental Pulmonary Hypertension." Circ. Res., v.94, pp. 1101-1108 (2004).
Schermuly et al., "Low-dose Systemic Phosphodiesterase Inhibitors Amplify the Pulmonary Vasodilatory Response to Inhaled Prostacyclin in Experimental Pulmonary Hypertension." Am. J. Respir. Crit. Care Med., v.160, pp. 1500-1506 (1999).
Sebkhi et al., "Phosphodiesterase Inhibition in the Treatment of Pulmonary Hypertension." Cardiovascular Reviews and Reports, v.23, pp. 274-279 (2002).
Travadi et al., "Phosphodiesterase Inhibitors for Persistent Pulmonary Hypertension of the Newborn: A Review." Pediatr. Pulmonol., v.36, pp. 529-535 (2003).
Wang and Wang, "Novel approaches to using PDE4 inhibitors for antihypertensive therapy." Current Opinion in Investigational Drugs, v.6:3, pp. 283-288 (2005).
Rabe, et al., "Identification of PDE isozymes in human pulmonary artery and effect of selective PDE inhibitors", Am. J. Physiol., vol. 266, pp. L536-L543, (1994).

(Continued)

*Primary Examiner* — Sreeni Padmanabhan
*Assistant Examiner* — Jody Karol
(74) *Attorney, Agent, or Firm* — Nath, Goldberg & Meyer; Sheldon M. McGee

(57) ABSTRACT

The invention relates to the use of Roflumilast, Roflumilast N-Oxide or a pharmaceutically acceptable salt of either for the treatment of pulmonary hypertension. The invention additionally relates to the use of Roflumilast, Roflumilast N-oxide or a pharmaceutically acceptable salt of either in combination with a PDE5 inhibitor or a pharmaceutically acceptable salt thereof for the treatment of pulmonary hypertension.

5 Claims, No Drawings

(56) References Cited

OTHER PUBLICATIONS

Schermuly, et al., "Subthreshold Doses of Specific Phosphodiesterase Type 3 and 4 Inhibitors Enhance the Pulmonary Vasodilatory Response to Nebulized Prostacyclin with Improvement in Gas Exchange", The Journal of Pharmacology and Experimental Therapeutics, vol. 292, No. 2, pp. 512-520, (2000).

P.R.M. Rocco, et al., "Therapeutic Potential of a New Phosphodiesterase Inhibitor in Acute Lung Injury", Eur. Respir. J., 2003, vol. 22, pp. 20-27.

* cited by examiner

ROFLUMILAST FOR THE TREATMENT OF PULMONARY HYPERTENSION

This application was filed under 35 U.S.C. 371 as a national stage of PCT/EP2006/061557, filed Apr. 12, 2006.

TECHNICAL FIELD

The invention relates to the use of Roflumilast, its pharmaceutically acceptable salts, its N-Oxide and the pharmaceutically acceptable salts of the latter for the preventive or curative treatment of pulmonary hypertension.

The invention furthermore relates to combinations of Roflumilast, its pharmaceutically acceptable salts, its N-Oxide and the pharmaceutically acceptable salts of the latter with PDE5 inhibitors; as well as to pharmaceutical compositions, combination products and kits containing these combinations and the use of such combinations in the treatment of pulmonary hypertension.

BACKGROUND OF THE INVENTION

In the international patent application WO9837894 the combination of phosphodiesterase inhibitors with adenylate cyclase agonists or guanylate cyclase agonists is disclosed for the treatment of inter alia pulmonary hypertension. In the international patent application WO9509636 a method for treating pulmonary hypertension is disclosed which comprises administering endotracheally or endobronchially to a subject an effective amount of a drug selected from the group consisting of cyclic nucleotides, phosphodiesterase inhibitors, nitric oxide precursors, nitric oxide donors and nitric oxide analogs, thereby decreasing pulmonary vascular resistance. In Cardiovasc. Rev & Rep 2002; 23, pp 274-279 Martin R. Wilkins et al review the use of phosphodiesterase inhibitors in the treatment of pulmonary hypertension. In Am J Physiol Lung Cell Mol Physiol 288: L103-L115, 2005 it is described that cAMP phosphodiesterase inhibitors potentiate effects of prostacyclin analogs in hypoxic pulmonary vascular remodelling. In Current Opinion in Investigational Drugs 2005 6(3), pp 283-288 Wang D et al describe novel approaches to use PDE4 inhibitors for antihypertensive therapy. In Current Opinion in Investigational Drugs 2002 3(8) Reid P describes that Roflumilast is metabolized in vivo to Roflumilast-N-oxide and that the both compounds behave in a similar manner in most test conditions. In the international patent application WO03070279 oral dosage forms containing a PDE4 inhibitor—exemplified exclusively by compositions comprising Roflumilast—for the treatment and prevention of all diseases regarded as treatable or preventable through the use of PDE4 inhibitors, including COPD are disclosed.

Pulmonary hypertension (PH) is defined by a mean pulmonary artery pressure (PAP) >25 mm Hg at rest or >30 mg Hg with exercise. According to current guidelines on diagnosis and treatment of pulmonary hypertension released by the European Society of Cardiology in 2004 (Eur Heart J 25: 2243-2278; 2004) clinical forms of PH are classified as (1) pulmonary arterial hypertension (PAH), (2) PH associated with left heart diseases, (3) PH associated with lung respiratory diseases and/or hypoxia, (4) PH due to chronic thrombotic and/or embolic disease, (5) PH of other origin (e.g. sarcoidosis). Group (1) is comprising e.g. idiopathic and familial PAH as well as PAH in the context of connective tissue disease (e.g. scleroderma, CREST), congenital systemic to pulmonary shunts, portal hypertension, HIV, intake of drugs and toxins (e.g. anorexigens). PH occurring in COPD was assigned to group (3). Muscularization of small (less than 500 μm diameter) pulmonary arterioles is widely accepted as a common pathological denominator of PAH (Group 1), however it may also occur in other forms of PH such as based on COPD or thrombotic and/or thrombembolic disease. Other pathoanatomical features in PH are thickening of the intima based on migration and proliferation of (myo) fibroblasts or smooth muscle cells and excessive generation of extracellular matrix, endothelial injury and/or proliferation and perivascular inflammatory cell infiltrates. Together, remodelling of distal pulmonary arterial vasculature results in augmented pulmonary vascular resistance, consecutive right heart failure and death. Whilst background therapy and more general measures such as oral anticoagulants, diuretics, digoxin or oxygen supply are still listed by current guidelines these remedies are not expected to interfere with causes or mechanisms of pulmonary arterial remodelling. Some patients with PAH may also benefit from $Ca^{++}$-antagonists in particular those with acute response to vasodilators. Innovative therapeutic approaches developed over the past decade considered molecular aberrations in particular enhanced endothelin-1 formation, reduced prostacyclin ($PGI_2$) generation and impaired eNOS activity in PAH vasculature. Endothelin-1 acting via $ET_A$-receptors is mitogenic for pulmonary arterial smooth muscle cells and triggers acute vasoconstriction. The oral $ET_A/ET_B$-antagonist Bosentan has recently been approved in the EU and United States for treatment of PAH after the compound demonstrated improvements in clinical endpoints such as mean PAP, PVR or 6 min walking test. However, Bosentan augmented liver enzymes and regular liver tests are mandatory. Currently selective $ET_A$ antagonists such as sitaxsentan or ambrisentan are under scrutiny.

As another strategy in management of PAH replacement of deficient prostacyclin by $PGI_2$ analogues such as epoprostenol, treprostinil, oral beraprost or iloprost emerged. Prostacyclin serves as a brake to excessive mitogenesis of vascular smooth muscle cells acting to augment cAMP generation. Intravenous prostacyclin (epoprostenol) significantly improved survival rates in idiopathic pulmonary hypertension as well as exercise capacity and was approved in North America and some European countries in the mid-1990s. However, owing to its short half-life epoprostenol has to be administered via continuous intravenous infusion that—whilst feasible—is uncomfortable, complicate and expensive. In addition, adverse events due to systemic effects of prostacyclin are frequent. Alternative prostacyclin analogues are treprostinil, recently approved in the United States for PAH treatment and delivered via continuous subcutaneous infusion and beraprost, the first biologically stable and orally active $PGI_2$ analogue, which has been approved for treatment of PAH in Japan. Its therapeutic profile appeared more favourable in patients with idiopathic PAH compared to other forms of pulmonary hypertension and side effects linked to systemic vasodilation following beraprost administration and local pain at the infusion site under treprostinil treatment are frequent. Administration of the prostacyclin analogue iloprost via the inhalative route was recently approved in Europe. Its beneficial effects on exercise capacity and haemodynamic parameters are to be balanced to a rather high dosing frequency comprising 6-12 courses of inhalation per day from appropriate devices.

Functional consequences of impaired endothelial nitric oxide formation as reported in pulmonary arterial hypertension may be overcome by selective inhibitors of phosphodiesterase-5 (PDE5) that is expressed in pulmonary artery smooth muscle cells. Consequently, the selective PDE5 inhibitor sildenafil was demonstrated to improve pulmonary haemodynamics and exercise capacity in PAH.

Most of these novel treatments primarily address smooth muscle cells function, however, in addition pulmonary vascular fibroblasts, endothelial cells but also perivascular macrophages and T-lymphocytes are considered to contribute to the development of pulmonary hypertension.

In spite of the different therapeutic approaches mentioned above the medical need to alleviate the disease burden in pulmonary hypertension is high. It is therefore an object of the present invention to make available pharmaceutical compositions for the preventive or curative treatment of pulmonary hypertension, which overcome some or all of the above-mentioned disadvantages.

DESCRIPTION OF THE INVENTION

Treatment of pulmonary hypertension can surprisingly be achieved by the use of a compound of formula 1.1

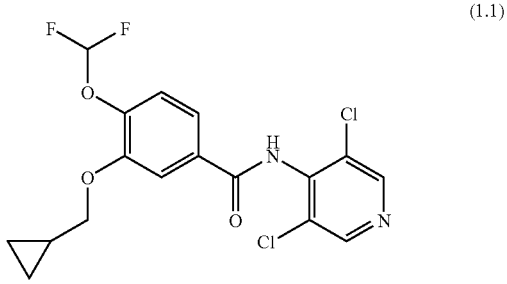 [SMILES: O=C(Nc1c(Cl)cncc1Cl)c1ccc(OC(F)F)c(OCC2CC2)c1]

(1.1)

or a pharmaceutically acceptable salt thereof and/or a compound of formula 1.2

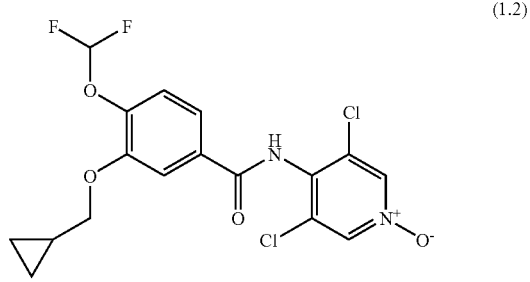 [SMILES: O=C(Nc1c(Cl)c[n+]([O-])cc1Cl)c1ccc(OC(F)F)c(OCC2CC2)c1]

(1.2)

or a pharmaceutically acceptable salt thereof.

The compound of formula 1.1 has the international non-proprietary name (INN) Roflumilast [3-cyclopropyl-methoxy-4-difluoromethoxy-N-(3,5-dichloropyrid-4-yl)benzamide].

The compound of formula 1.2 is Roflumilast-N-Oxide [3-cyclopropylmethoxy-4-difluoromethoxy-N-(3,5-dichloro-1-oxido-pyridin-4-yl)benzamide].

The preparation of Roflumilast, its pharmaceutically acceptable salts and its N-Oxide as well as the use of these compounds as PDE4 inhibitors is described in the international patent application WO9501338.

Salts encompassed within the term "pharmaceutically acceptable salts" of compounds of formulae 1.1 and 1.2 refer to non-toxic salts of these compounds which are generally prepared by reacting a free base with a suitable organic or inorganic acid or by reacting an acid with a suitable organic or inorganic base. Particular mention may be made of the pharmaceutically acceptable inorganic and organic acids customarily used in pharmacy. Those suitable are in particular water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid. As examples of pharmaceutically acceptable salts with bases may be mentioned the lithium, sodium, potassium, calcium, aluminium, magnesium, titanium, ammonium, meglumine or guanidinium salts.

It is understood that the compounds of formulae 1.1 and 1.2 and their pharmaceutically acceptable salts can also be present in the form of their pharmaceutically acceptable solvates and in particular in the form of their hydrates.

The expression "pulmonary hypertension" as used herein comprises different forms of pulmonary hypertension. Non-limiting examples, which may be mentioned in this connection are idiopathic pulmonary arterial hypertension; familial pulmonary arterial hypertension; pulmonary arterial hypertension associated with collagen vascular disease, congenital systemic-to-pulmonary shunts, portal hypertension, HIV infection, drugs or toxins; pulmonary hypertension associated with thyroid disorders, glycogen storage disease, Gaucher disease, hereditary hemorrhagic telangiectasia, hemoglobinopathies, myeloproliferative disorders or splenectomy; pulmonary arterial hypertension associated with pulmonary capillary hemangiomatosis; persistent pulmonary hypertension of the newborn; pulmonary hypertension associated with chronic obstructive pulmonary disease, interstitial lung disease, hypoxia driven alveolar hypoventilation disorders, hypoxia driven sleep-disordered breathing or chronic exposure to high altitude; pulmonary hypertension associated with development abnormalities; and pulmonary hypertension due to thromboembolic obstruction of distal pulmonary arteries.

The term "effective amount" refers to a therapeutically effective amount of the compound of formula 1.1 or the compound of formula 1.2 for the preventive or curative treatment of pulmonary hypertension. In case of a combination therapy the term "effective amount" refers to the sum of the amounts of the combination partners, which is therapeutically effective for the preventive or curative treatment of pulmonary hypertension.

"Patient" includes both human and other mammals.

It has now been found that Roflumilast reduces the pulmonary arterial pressure (PAP), the right ventricular hypertrophy and the distal muscularization in chronic pulmonary hypertension induced by hypoxia or monocrotalin in rats, while systemic arterial pressure and heart rate remained unaffected.

Thus, a first aspect of the present invention is the use of a compound selected from the group consisting of Roflumilast, a pharmaceutically acceptable salt of Roflumilast, Roflumilast-N-Oxide and a pharmaceutically acceptable salt of Roflumilast-N-Oxide for the production of a pharmaceutical composition for the preventive or curative treatment of pulmonary hypertension.

In a second aspect the present invention relates to a method for the preventive or curative treatment of pulmonary hypertension in a patient comprising administering to said patient in need thereof an effective amount of a compound selected from the group consisting of Roflumilast, a pharmaceutically acceptable salt of Roflumilast, Roflumilast-N-Oxide and a pharmaceutically acceptable salt of Roflumilast-N-Oxide.

As mentioned above, the expression "pulmonary hypertension" as used herein comprises different forms of pulmonary hypertension. Another aspect of the present invention therefore is the use of a compound selected from the group consisting of Roflumilast, a pharmaceutically acceptable salt of Roflumilast, Roflumilast-N-Oxide and a pharmaceutically acceptable salt of Roflumilast-N-Oxide for the production of a pharmaceutical composition for the preventive or curative treatment of a form of pulmonary hypertension selected from the group of idiopathic pulmonary arterial hypertension; familial pulmonary arterial hypertension; pulmonary arterial hypertension associated with collagen vascular disease, congenital systemic-to-pulmonary shunts, portal hypertension, HIV infection, drugs or toxins; pulmonary hypertension associated with thyroid disorders, glycogen storage disease, Gaucher disease, hereditary hemorrhagic telangiectasia, hemoglobinopathies, myeloproliferative disorders or splenectomy; pulmonary arterial hypertension associated with pulmonary capillary hemangiomatosis; persistent pulmonary hypertension of the newborn; pulmonary hypertension associated with chronic obstructive pulmonary disease, interstitial lung disease, hypoxia driven alveolar hypoventilation disorders, hypoxia driven sleep-disordered breathing or chronic exposure to high altitude; pulmonary hypertension associated with development abnormalities; and pulmonary hypertension due to thromboembolic obstruction of distal pulmonary arteries.

In still another aspect the present invention relates to a method for the preventive or curative treatment of a form of pulmonary hypertension in a patient comprising administering to said patient in need thereof an effective amount of a compound selected from the group consisting of Roflumilast, a pharmaceutically acceptable salt of Roflumilast, Roflumilast-N-Oxide and a pharmaceutically acceptable salt of Roflumilast-N-Oxide, wherein the manifestation of pulmonary hypertension is selected from the group of idiopathic pulmonary arterial hypertension; familial pulmonary arterial hypertension; pulmonary arterial hypertension associated with collagen vascular disease, congenital systemic-to-pulmonary shunts, portal hypertension, HIV infection, drugs or toxins; pulmonary hypertension associated with thyroid disorders, glycogen storage disease, Gaucher disease, hereditary hemorrhagic telangiectasia, hemoglobinopathies, myeloproliferative disorders or splenectomy; pulmonary arterial hypertension associated with pulmonary capillary hemangiomatosis; persistent pulmonary hypertension of the newborn; pulmonary hypertension associated with chronic obstructive pulmonary disease, interstitial lung disease, hypoxia driven alveolar hypoventilation disorders, hypoxia driven sleep-disordered breathing or chronic exposure to high altitude; pulmonary hypertension associated with development abnormalities; and pulmonary hypertension due to thromboembolic obstruction of distal pulmonary arteries.

Roflumilast, Roflumilast-N-oxide or a pharmaceutically acceptable salt of either may be administered to a patient in need of treatment in any of the generally accepted modes of administration available in the art. Illustrative examples of suitable modes of administration include oral, intravenous, nasal, parenteral, transdermal and rectal delivery as well as administration by inhalation. The most preferred mode of administration of Roflumilast, Roflumilast-N-oxide or a pharmaceutically acceptable salt of either is oral. In another preferred embodiment Roflumilast, Roflumilast-N-oxide or a pharmaceutically acceptable salt of either is administered by intravenous infusion or injection. In a further preferred embodiment Roflumilast, Roflumilast-N-oxide or a pharmaceutically acceptable salt of either is administered by inhalation.

Typically, the Roflumilast, Roflumilast-N-oxide or a pharmaceutically acceptable salt of either will be administered in the form of a pharmaceutical composition comprising Roflumilast, Roflumilast-N-oxide or a pharmaceutically acceptable salt of either in conjunction with at least one pharmaceutically acceptable auxiliary.

The pharmaceutical compositions are prepared by processes which are known per se and familiar to the person skilled in the art. As pharmaceutical compositions Roflumilast, Roflumilast-N-oxide or a pharmaceutically acceptable salt of either is either employed as such, or preferably in combination with at least one pharmaceutically acceptable auxiliary, e. g. in the form of tablets, coated tablets, capsules, caplets, suppositories, emulsions, suspensions, gels or solutions, the active compound content advantageously being between 0.1 to 99.9 wt %, preferably 5 to 95 wt %, more preferably 20 to 80 wt % and where, by the appropriate choice of the auxiliaries, a pharmaceutical administration form (e.g. a sustained-release form or an enteric form) exactly suited to the active compound and/or to the desired onset of action can be achieved.

The person skilled in the art is familiar on the basis of his/her expert knowledge with auxiliaries, which are suitable for the desired pharmaceutical formulations. As pharmaceutically acceptable auxiliaries, any auxiliaries known to be suitable for preparing pharmaceutical compositions can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

Suitable oral dosage forms of Roflumilast and Roflumilast-N-Oxide are described in the international patent application WO03070279.

Roflumilast or Roflumilast-N-Oxide can also be administered in the form of an aerosol; the aerosol particles of solid, liquid or mixed composition preferably having a diameter of 0.5 to 10 μm, advantageously of 2 to 6 μm. Aerosol generation can be carried out, for example, by pressure-driven jet atomizers or ultrasonic atomizers, by propellant-driven metered aerosols or propellant-free administration of micronized active compounds from inhalation capsules.

Depending on the inhaler system used, in addition to the active compounds the administration forms additionally contain the required auxiliaries, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of devices are available with which aerosols of optimum particle size can be generated and administered, using an inhalation technique which is as right as possible for the patient. In addition to the use of adaptors (spacers, expanders) and pear-shaped containers (e.g. Nebulator®), Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP0505321), using which an optimal administration of active compound can be achieved.

It is known to the person skilled in the art that the optimum dose of an active compound can vary as a function of body weight, the age and the general condition of the patient, and his/her response behaviour to the active compound.

In case of oral administration of 3-cyclopropylmethoxy-4-difluoromethoxy-N-(3,5-dichloropyrid-4-yl)benzamide (Roflumilast), the daily dose (for an adult patient) is in the range from 50-1000 μg, preferably in the range from 50-500 μg, more preferably in the range of 250-500 μg, preferably by once daily administration.

In case of intravenous administration of 3-cyclopropyl-methoxy-4-difluoromethoxy-N-(3,5-dichloropyrid-4-yl) benzamide (Roflumilast), the daily dose (for an adult patient) is in the range from 50-500 μg, preferably in the range from 150-300 μg.

For the treatment of pulmonary hypertension Roflumilast, pharmaceutically acceptable salts of Roflumilast, Roflumilast-N-Oxide or pharmaceutically acceptable salts of Roflumilast-N-Oxide may be administered in combination with PDE5 inhibitors or pharmaceutically acceptable salts thereof.

Non-limiting examples of PDE5 inhibitors which may be used according to the invention in combination with Roflumilast, pharmaceutically acceptable salts of Roflumilast, Roflumilast-N-Oxide or pharmaceutically acceptable salts of Roflumilast-N-Oxide are provided in the following Table 1.

TABLE 1

| INN or Research Code | Structure/Chemical Name |
| --- | --- |
| SILDENAFIL | 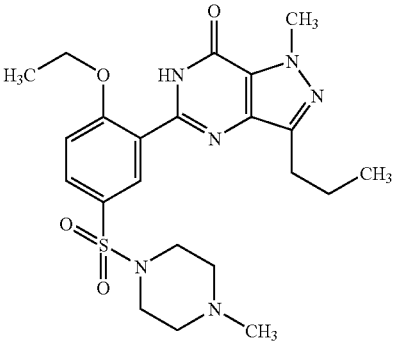<br>5-{2-ethoxy-5-[(4-methylpiperazin-1-yl)sulfonyl]phenyl}-1-methyl-3-propyl-1,6-dihydro-7H-pyrazolo[4,3-d]pyrimidin-7-one |
| TADALAFIL | 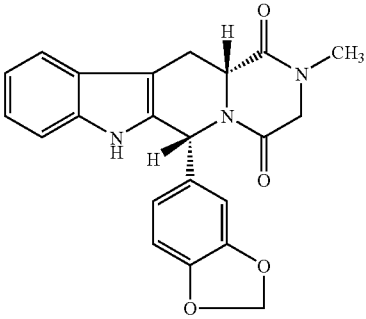<br>(6R,12aR)-6-(1,3-benzodioxol-5-yl)-2-methyl-2,3,6,7,12,12a-hexahydropyrazino[1′,2′:1,6]pyrido[3,4-b]indole-1,4-dione |
| VARDENAFIL | 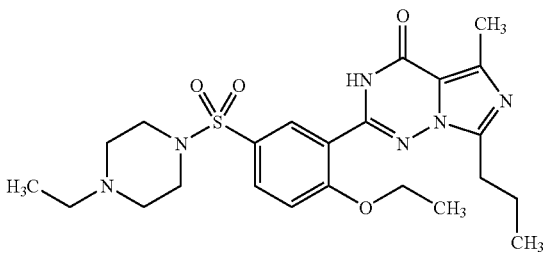<br>2-{2-ethoxy-5-[(4-ethylpiperazin-1-yl)sulfonyl]phenyl}-5-methyl-7-propylimidazo[5,1-f][1,2,4]triazin-4(3H)-one |

TABLE 1-continued

| INN or Research Code | Structure/Chemical Name |
|---|---|
| UK-343664 | 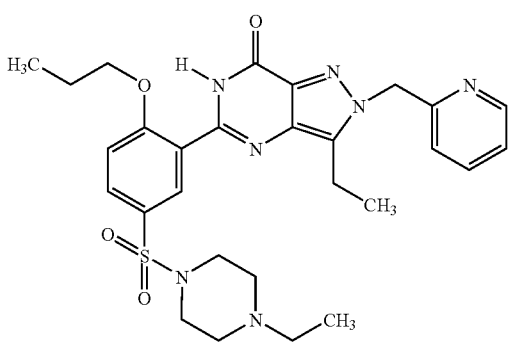<br>3-ethyl-5-{5-[(4-ethylpiperazin-1-yl)sulfonyl]-2-propoxyphenyl}-2-(pyridin-2-ylmethyl)-2,6-dihydro-7H-pyrazolo[4,3-d]pyrimidin-7-one |
| UK-357903 | 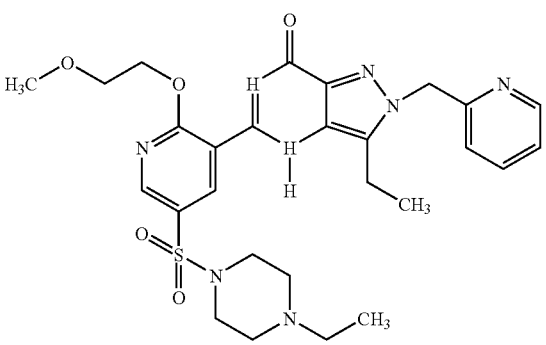<br>3-ethyl-5-{5-[(4-ethylpiperazin-1-yl)sulfonyl]-2-(2-methoxy)pyridin-3-yl}-2-(pyridin-2-ylmethyl)-2,4-dihydro-7H-pyrazolo[4,3-d]pyrimidin-7-one |
| UK-371800 | 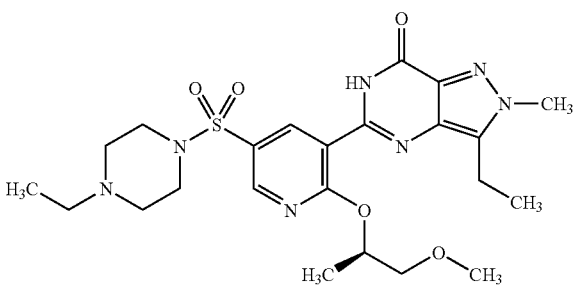<br>3-ethyl-5-{5-[(4-ethylpiperazin-1-yl)sulfonyl]-2-[(1R)-2-methoxy-1-methylethoxy]pyridin-3-yl}-2-methyl-2,6-dihydro-7H-pyrazolo[4,3-d]pyrimidin-7-one |
| AVANAFIL | 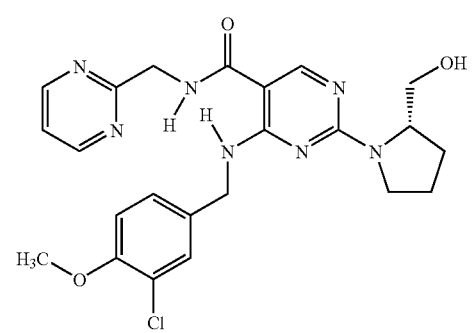<br>4-[(3-chloro-4-methoxybenzyl)amino]-2-[(2s)-2-(hydroxymethyl)pyrrolidin-1-yl]-N-(pyrimidin-2-ylmethyl)pyrimidine-5-carbozamide |

TABLE 1-continued

| INN or Research Code | Structure/Chemical Name |
|---|---|
| BEMINAFIL | 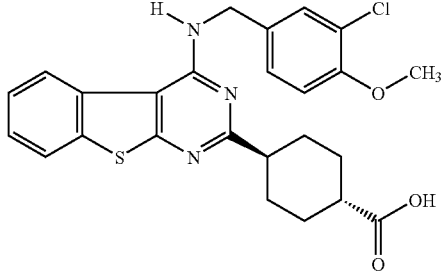<br>trans-4-{4-[(3-chloro-4-methoxybenzyl)amino][1]benzothieno[2,3-d]pyrimidin-2-yl}cyclohexanecarboxylic acid |
| DASANTAFIL | 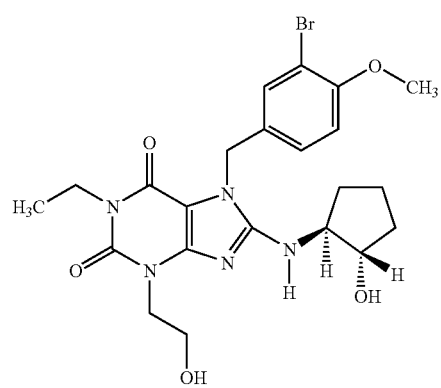<br>7-(3-bromo-4-methoxybenzyl)-1-ethyl-8-{[(1S,2S)-2-hydroxycyclopentyl]amino}-3-(2-hydroxyethyl)-3,7-dihydro-1H-purine-2,6-dione |
| UDENAFIL | 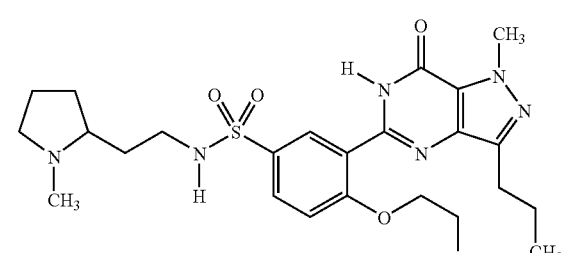<br>3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-porpoxybenzenesulfonamide |
| BMS-341400 | 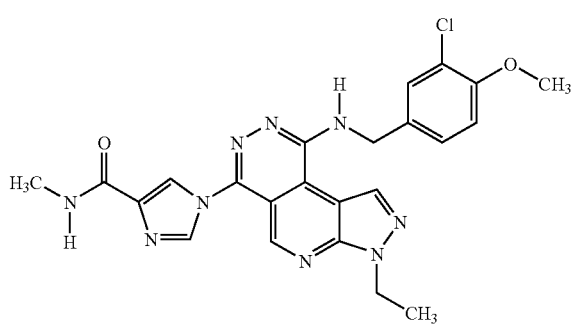<br>1-{9-[(3-chloro-4-methoxybenzyl)amino]-3-ethyl-3H-pyrazolo[4',3':5,6]pyrido[3,4-d]pyridazin-6-yl}-N-methyl-1H-imidazole-4-carboxamide |

Further aspects of the present invention are therefore:

Compositions comprising an amount of a compound selected from the group consisting of Roflumilast, a pharmaceutically acceptable salt of Roflumilast, Roflumilast-N-Oxide and a pharmaceutically acceptable salt of Roflumilast-N-Oxide, and an amount of a PDE5 inhibitor or a pharmaceutically acceptable salt thereof, wherein the first amount and the second amount together comprise an effective amount for the preventive or curative treatment of pulmonary hypertension.

Another aspect of the present invention provides the use of the above-mentioned compositions in the preventive or curative treatment of pulmonary hypertension.

In still another aspect the present invention provides the use of a compound selected from the group consisting of Roflumilast, a pharmaceutically acceptable salt of Roflumilast, Roflumilast-N-Oxide and a pharmaceutically acceptable salt of Roflumilast-N-Oxide in combination with a PDE5 inhibitor or a pharmaceutically acceptable salt thereof for the production of a pharmaceutical composition, combination product or kit for the preventive or curative treatment of pulmonary hypertension.

Roflumilast, a pharmaceutically acceptable salt of Roflumilast, Roflumilast-N-Oxide or a pharmaceutically acceptable salt of Roflumilast-N-Oxide and the PDE5 inhibitor or a pharmaceutically acceptable salt thereof can be administered simultaneously, sequentially or separately. To this effect, the active compounds of the combination can be formulated in a single formulation (pharmaceutical composition) or in separate formulations (combination product or kit).

Therefore, according to a further aspect of the present invention there is provided a pharmaceutical composition comprising a pharmaceutical formulation including an amount of a compound selected from the group consisting of Roflumilast, a pharmaceutically acceptable salt of Roflumilast, Roflumilast-N-Oxide and a pharmaceutically acceptable salt of Roflumilast-N-Oxide, an amount of a PDE5 inhibitor or a pharmaceutically acceptable salt thereof, wherein the first amount and the second amount together comprise an effective amount for the preventive or curative treatment of pulmonary hypertension, and at least one pharmaceutically acceptable auxiliary.

The above-mentioned pharmaceutical composition provides for the administration of Roflumilast, a pharmaceutically acceptable salt of Roflumilast, Roflumilast-N-Oxide or a pharmaceutically acceptable salt of Roflumilast-N-Oxide in admixture with a PDE5 inhibitor or a pharmaceutically acceptable salt thereof and is thus presented as a single formulation.

Alternatively, Roflumilast, a pharmaceutically acceptable salt of Roflumilast, Roflumilast-N-Oxide or a pharmaceutically acceptable salt of Roflumilast-N-Oxide and the PDE5 inhibitor or a pharmaceutically acceptable salt thereof may be presented as separate formulations, wherein at least one of those formulations comprises Roflumilast, a pharmaceutically acceptable salt of Roflumilast, Roflumilast-N-Oxide or a pharmaceutically acceptable salt of Roflumilast-N-Oxide and at least one comprises a PDE5 inhibitor or a pharmaceutically acceptable salt thereof.

Thus, there is further provided:

A combination product comprising the components: (A) an amount of a compound selected from the group consisting of Roflumilast, a pharmaceutically acceptable salt of Roflumilast, Roflumilast-N-Oxide and a pharmaceutically acceptable salt of Roflumilast-N-Oxide; (B) an amount of a PDE5 inhibitor or a pharmaceutically acceptable salt thereof; wherein the first and the second amount together comprise an effective amount for the treatment of pulmonary hypertension and wherein each of the components (A) and (B) is formulated in admixture with at least one pharmaceutically acceptable auxiliary.

A kit comprising the components: (A) a pharmaceutical formulation including an amount of a compound selected from the group consisting of Roflumilast, a pharmaceutically acceptable salt of Roflumilast, Roflumilast-N-Oxide and a pharmaceutically acceptable salt of Roflumilast-N-Oxide, in admixture with at least one pharmaceutically acceptable auxiliary; (B) a pharmaceutical formulation including an amount of a PDE5 inhibitor or a pharmaceutically acceptable salt thereof, in admixture with at least one pharmaceutically acceptable auxiliary; wherein the first and the second amount together comprise an effective amount for the treatment of pulmonary hypertension.

Simultaneous administration of Roflumilast, a pharmaceutically acceptable salt of Roflumilast, Roflumilast-N-Oxide or a pharmaceutically acceptable salt of Roflumilast-N-Oxide and a PDE5 inhibitor or a pharmaceutically acceptable salt thereof can be accomplished, by administering to the patient in need of pulmonary hypertension therapy the pharmaceutical composition according to the invention in one dosage form, such as for example in a single capsule, tablet or injection.

Components (A) and (B) of the combination product as well as of the kit may be administered sequentially or separately over the course of the treatment of pulmonary hypertension.

Sequential or separate administration of Roflumilast, a pharmaceutically acceptable salt of Roflumilast, Roflumilast-N-Oxide or a pharmaceutically acceptable salt of Roflumilast-N-Oxide and a PDE5 inhibitor or a pharmaceutically acceptable salt thereof can be accomplished, by administering to the patient in need of pulmonary hypertension therapy components (A) and (B) of the combination product or the kit according to the invention in (multiple) separate dosage forms, such as for example, in separate capsules, tablets or injections.

In an alternative, one of the components (A) and (B) may be formulated as tablet or capsule and the other component may be formulated for administration, for example, by injection or inhalation.

Sequential administration encompasses a short period between the administration of components (A) and (B) of the combination product or the kit according to the invention (for example, the time that is needed to swallow one tablet after the other).

Separate administration encompasses both relatively short and relatively long periods between the administration of components (A) and (B) of the combination product or the kit according to the invention.

However, for the purposes of the present invention at least one of the components is administered while the other component is still having an effect on the patient being treated. In a preferred embodiment of the invention the effect on the patient being treated is a synergistic effect.

The combined administration of Roflumilast, a pharmaceutically acceptable salt of Roflumilast, Roflumilast-N-Oxide or a pharmaceutically acceptable salt of Roflumilast-N-Oxide and a PDE5 inhibitor or a pharmaceutically acceptable salt thereof, either in form of the pharmaceutical composition, combination product or kit according to the invention, lead to an effective treatment of pulmonary hypertension, and in a preferred embodiment is superior to the use of either agent alone. Moreover, in a particularly preferred embodiment, the combined administration of Roflumilast, a pharmaceutically acceptable salt of Roflumilast, Roflumilast-N-Oxide or a pharmaceutically acceptable salt of Roflumilast-N-Oxide and a PDE5 inhibitor or a pharmaceutically acceptable salt thereof shows a synergistic efficacy for treating pulmonary hypertension.

As used herein, the term "synergistic" refers to the combination of Roflumilast, a pharmaceutically acceptable salt of Roflumilast, Roflumilast-N-Oxide or a pharmaceutically acceptable salt of Roflumilast-N-Oxide with a PDE5 inhibitor or a pharmaceutically acceptable salt thereof either in form of the pharmaceutical composition, combination product or kit according to the invention having an efficacy for the treatment of pulmonary hypertension that is greater than would be expected from the sum of their individuals effects. The synergistic effects of the embodiments of the present invention encompass additional unexpected advantages for the treatment of pulmonary hypertension. Such additional advantages may include, but are not limited to, lowering the required dose of one or more of the active compounds of the combination, reducing the side effects of one or more of the active compounds of the combination or rendering one or more of the active compounds more tolerable to the patient in need of pulmonary hypertension therapy.

The combined administration of Roflumilast, a pharmaceutically acceptable salt of Roflumilast, Roflumilast-N-Oxide or a pharmaceutically acceptable salt of Roflumilast-N-Oxide and a PDE5 inhibitor or a pharmaceutically acceptable salt thereof may also be useful for decreasing the required number of separate dosages, thus, potentially improving compliance of the patient in need of pulmonary hypertension therapy.

A further aspect of the present invention is the use of a pharmaceutical composition, a pharmaceutical combination or a kit according to the invention for the production of a medicament for the preventive or curative treatment of pulmonary hypertension.

Still a further aspect of the present invention is a method for the preventive or curative treatment of pulmonary hypertension comprising administering to a patient in need thereof a pharmaceutical composition comprising a pharmaceutical formulation including an amount of a compound selected from the group consisting of Roflumilast, a pharmaceutically acceptable salt of Roflumilast, Roflumilast-N-Oxide and a pharmaceutically acceptable salt of Roflumilast-N-Oxide, an amount of a PDE5 inhibitor or a pharmaceutically acceptable salt thereof, wherein the first amount and the second amount together comprise an effective amount for the preventive and curative treatment of pulmonary hypertension, and at least one pharmaceutically acceptable auxiliary.

Another aspect of the present invention is a method for the preventive and curative treatment of pulomonary hypertension comprising administering to a patient in need thereof a combination product comprising the components:

(A) an amount of a compound selected from the group consisting of Roflumilast, a pharmaceutically acceptable salt of Roflumilast, Roflumilast-N-Oxide and a pharmaceutically acceptable salt of Roflumilast-N-Oxide;

(B) an amount of a PDE5 inhibitor or a pharmaceutically acceptable salt thereof;

wherein the first and the second amount together comprise an effective amount for the preventive or curative treatment of pulmonary hypertension;

wherein each of the components (A) and (B) is formulated in admixture with at least one pharmaceutically acceptable auxiliary;

and wherein the components (A) and (B) are administered sequentially or separately.

As already mentioned above non-limiting examples of PDE5 inhibitors which may be useful employed in the pharmaceutical compositions, combination products and kits according to the invention are listed in Table 1.

In one embodiment of the present invention the PDE5 inhibitor which is employed in the pharmaceutical compositions, combination products or kits according to the invention is selected from the group consisting of SILDENAFIL (CAS-No. 139755-83-2), TADALAFIL (CAS-No. 171596-29-5), VARDENAFIL (CAS-No. 224785-90-4), UK-343664 (CAS-No. 215297-27-1), UK-357903 (CAS-No. 247580-98-9), UK-371800 (CAS-No. 247582-13-4), AVANAFIL (CAS-No. 330784-47-9), BEMINAFIL (CAS-No. 566906-50-1), DASANTA-FIL (CAS-No. 405214-79-1), UDENAFIL (CAS-No. 268203-93-6), BMS-341400 (Cas-No. 296250-53-8) and the pharmaceutically acceptable salts of these compounds.

In one embodiment of the present invention the PDE5 inhibitor which is employed in the pharmaceutical compositions, combination products or kits according to the invention is SILDENAFIL or a pharmaceutically acceptable salt thereof.

In another embodiment of the present invention the pharmaceutically acceptable salts of SILDENAFIL are the hemicitrate, the citrate or the mesylate salt of SILDENAFIL.

In another embodiment of the present invention the PDE5 inhibitor which is employed in the pharmaceutical compositions, combination products or kits according to the invention is TADALAFIL or a pharmaceutically acceptable salt thereof.

In another embodiment of the present invention the PDE5 inhibitor which is employed in the pharmaceutical compositions, combination products or kits according to the invention is VARDENAFIL or a pharmaceutically acceptable salt thereof.

In another embodiment of the present invention the pharmaceutically acceptable salts of VARDENAFIL are the mono-hydrochloride salt or the di-hydrochloride salt of VARDENAFIL.

In another embodiment of the present invention the PDE5 inhibitor which is employed in the pharmaceutical compositions, combination products or kits according to the invention is UK-343664 or a pharmaceutically acceptable salt thereof.

In another embodiment of the present invention the PDE5 inhibitor which is employed in the pharmaceutical compositions, combination products or kits according to the invention is UK-357903 or a pharmaceutically acceptable salt thereof.

In another embodiment of the present invention the PDE5 inhibitor which is employed in the pharmaceutical compositions, combination products or kits according to the invention is UK-371800 or a pharmaceutically acceptable salt thereof.

In another embodiment of the present invention the PDE5 inhibitor which is employed in the pharmaceutical compositions, combination products or kits according to the invention is AVANAFIL or a pharmaceutically acceptable salt thereof.

In another embodiment of the present invention the pharmaceutically acceptable salt of AVANAFIL is the besilate salt of AVANAFIL.

In another embodiment of the present invention the PDE5 inhibitor which is employed in the pharmaceutical compositions, combination products or kits according to the invention is BEMINAFIL or a pharmaceutically acceptable salt thereof.

In another embodiment of the present invention the pharmaceutically acceptable salts of BEMINAFIL are the sodium or the ethanolamine salt of BEMINAFIL.

In another embodiment of the present invention the PDE5 inhibitor which is employed in the pharmaceutical compositions, combination products or kits according to the invention is DASANTAFIL or a pharmaceutically acceptable salt thereof.

In another embodiment of the present invention the PDE5 inhibitor which is employed in the pharmaceutical compositions, combination products or kits according to the invention is UDENAFIL or a pharmaceutically acceptable salt thereof.

In another embodiment of the present invention the PDE5 inhibitor which is employed in the pharmaceutical compositions, combination products or kits according to the invention is BMS-341400 or a pharmaceutically acceptable salt thereof.

Additional information with regard to the preparation, suitable dosage forms and dose ranges of the PDE5 inhibitors listed in Table 1 can be found in the following patents/patent applications: EP0463756, WO2004072079, EP1097711, EP0967214, EP1049695, WO03011262, EP0740668, WO9849166, EP1073658, WO9954333, EP1219609, WO9955708, WO0224698, WO0027848 and EP1165521.

"Pharmaceutically acceptable salts" of the PDE5 inhibitors are not limited to the examples given above. The term refers to non-toxic salts of these compounds. These pharmaceutically acceptable salts are generally prepared by reacting a free base with a suitable organic or inorganic acid or by reacting an acid with a suitable organic or inorganic base. Particular mention may be made of the pharmaceutically acceptable inorganic and organic acids customarily used in pharmacy. Those suitable are in particular water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 1-hydroxy-2-naphthoic acid. As examples of pharmaceutically acceptable salts with bases may be mentioned the lithium, sodium, potassium, calcium, aluminium, magnesium, titanium, ammonium, meglumine or guanidinium salts.

It is understood that the PDE5 inhibitors and their pharmaceutically acceptable salts can also be present in the form of their pharmaceutically acceptable solvates, and in particular in the form of their hydrates.

Mode of administration, dosage forms and dosage of the combinations:

The combinations according to the invention may be administered to a patient in need of treatment in any of the generally accepted modes of administration available in the art. Illustrative examples of suitable modes of administration include oral, intravenous, nasal, parenteral, transdermal and rectal delivery as well as administration by inhalation.

Tablets, coated tablets (dragees), pills, cachets, capsules (caplets), granules, solutions, emulsions and suspensions are e.g. suitable for oral administration. In particular, said formulations can be adapted so as to represent, for example, an enteric form, an immediate release form, a delayed release form, a repeated dose release form, a prolonged release form or a sustained release form. Said forms can be obtained, for example, by coating tablets, by dividing tablets into several compartments separated by layers disintegrating under different conditions (e.g. pH conditions) or by coupling the active compound to a biodegradable polymer.

Administration by inhalation is preferably made by using an aerosol; the aerosol particles of solid, liquid or mixed composition preferably having a diameter of 0.5 to 10 μm, advantageously of 2 to 6 μm. Aerosol generation can be carried out, for example, by pressure-driven jet atomizers or ultrasonic atomizers, by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of devices are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP0505321), using which an optimal administration of active compound can be achieved.

The pharmaceutical compositions (formulations) comprising Roflumilast, Roflumilast-N-oxide or a pharmaceutically acceptable salt of either and/or a PDE5 inhibitor or a pharmaceutically acceptable salt thereof and at least one pharmaceutically acceptable auxiliary can be manufactured in a manner known to a person skilled in the art, e. g. by dissolving, mixing, granulating, dragee-making, levigating, emulsifying, encapsulating, entrapping or lyophilizing processes.

As pharmaceutically acceptable auxiliaries, any auxiliaries known to be suitable for preparing pharmaceutical compositions (formulations) can be used. Examples thereof include, but are not limited to, solvents, excipients, dispersants, emulsifiers, solubilizers, gel formers, ointment bases, antioxidants, preservatives, stabilizers, carriers, fillers, binders, thickeners, complexing agents, disintegrating agents, buffers, permeation promoters, polymers, lubricants, coating agents, propellants, tonicity adjusting agents, surfactants, colorants, flavorings, sweeteners and dyes. In particular, auxiliaries of a type appropriate to the desired formulation and the desired mode of administration are used.

For intravenous administration, preferably solutions (e.g. sterile solutions, isotonic solutions) are used.

The preferred mode of administration of the combinations according to the invention depend on the specific combination partners.

As mentioned above Roflumilast, Roflumilast-N-oxide or a pharmaceutically acceptable salt of either may be administered in a variety of forms. These include, for example, liquid, semi-solid and solid dosage forms, such as liquid solutions (e.g. injectable and infusible solutions) dispersions or suspensions, tablets, pills, powders, liposomes or suppositories. The preferred form depends on the intended mode of administration and the combination partner.

The most preferred mode of administration of Roflumilast, Roflumilast-N-oxide or a pharmaceutically acceptable salt of either is oral. In another preferred embodiment Roflumilast, Roflumilast-N-oxide or a pharmaceutically acceptable salt of either is administered by intravenous infusion or injection. In a further preferred embodiment Roflumilast, Roflumilast-N-oxide or a pharmaceutically acceptable salt of either is administered by inhalation.

PDE5 inhibitors or the pharmaceutically acceptable salts thereof used in the combinations according to the invention can also be administered in any of the accepted modes of administration available in the art. The preferred mode of administration of the PDE5 inhibitors or the pharmaceutically acceptable salts thereof is oral.

The citrate salt of SILDENAFIL is the preferred salt for oral administration of Sildenafil, however other pharmaceutically acceptable salts may also be used. SILDENAFIL can also be administered by inhalation. A preferred formulation of SILDENAFIL for administration by inhalation comprises an aqueous formulation of SILDENAFIL mesylate for use in an aerosol nebulizer or atomizer.

As part of the combination therapy according to the invention Roflumilast, Roflumilast-N-oxide or a pharmaceutically acceptable salt of either and the PDE5 inhibitor or a pharmaceutically acceptable salt thereof are dosed in an order of magnitude customary for the mono-therapy, it more likely being possible, on account of the individual actions, which are mutually positively influencing and reinforcing, to reduce the respective doses on the combined administration of Roflumilast, Roflumilast-N-oxide or a pharmaceutically acceptable salt of either and the PDE5 inhibitor or a pharmaceutically acceptable salt thereof with the norm.

As mentioned above in the case of oral administration of 3-cyclopropylmethoxy-4-difluoromethoxy-N-(3,5-dichloropyrid-4-yl)benzamide (Roflumilast), the daily dose (for an adult patient) is in the range from 50 to 1000 µg, preferably in the range from 50 to 500 µg, more preferably in the range of 250 to 500 µg, preferably by once daily administration. In the case of intravenous administration of 3-cyclopropylmethoxy-4-difluoromethoxy-N-(3,5-dichloropyrid-4-yl)benzamide (Roflumilast) the daily dose (for an adult patient) is in the range from 50 to 500 µg per day, preferably in the range of 150 to 300 µg per day.

For oral and parenteral administration to human patients, the daily dosage level (for an adult patient) of the PDE5 inhibitors or the pharmaceutically acceptable salts thereof will usually be in a range of 1 to 500 mg, preferably in the range of 1 to 200 mg, more preferably in the range of 1 to 100 mg (in single or divided doses).

In case of the PDE5 inhibitors TADALAFIL, VARDENAFIL and SILDENAFIL the daily dosage level (for an adult patient) will preferably be up to 100 mg, more preferably up to 50 mg, more preferably up to 20 mg (in single or divided doses).

In case of Sildenafil the currently approved dose for the treatment of pulmonary hypertension is 20 mg Sildenafil (in form of an oral tablet containing Sildenafil citrate) three times a day.

TABLE 2

Preferred Combinations

| Example Number | Combination | |
|---|---|---|
| 1 | Roflumilast | SILDENAFIL |
| 2 | Roflumilast-N-Oxide | SILDENAFIL |
| 3 | Roflumilast | SILDENAFIL citrate |
| 4 | Roflumilast-N-Oxide | SILDENAFIL citrate |
| 5 | Roflumilast | SILDENAFIL hemi-citrate |
| 6 | Roflumilast-N-Oxide | SILDENAFIL hemi-citrate |
| 7 | Roflumilast | SILDENAFIL mesylate |
| 8 | Roflumilast-N-Oxide | SILDENAFIL mesylate |
| 9 | Roflumilast | VARDENAFIL |
| 10 | Roflumilast-N-Oxide | VARDENAFIL |
| 11 | Roflumilast | VARDENAFIL hydrochloride |
| 12 | Roflumilast-N-Oxide | VARDENAFIL hydrochloride |
| 13 | Roflumilast | VARDENAFIL dihydrochloride |
| 14 | Roflumilast-N-Oxide | VARDENAFIL dihydrochloride |
| 15 | Roflumilast | TADALAFIL |
| 16 | Roflumilast-N-Oxide | TADALAFIL |
| 17 | Roflumilast | UK-343664 |
| 18 | Roflumilast-N-Oxide | UK-343664 |
| 19 | Roflumilast | UK-357903 |
| 20 | Roflumilast-N-Oxide | UK-357903 |
| 21 | Roflumilast | UK-371800 |
| 22 | Roflumilast-N-Oxide | UK-371800 |
| 23 | Roflumilast | AVANAFIL |
| 24 | Roflumilast-N-Oxide | AVANAFIL |
| 25 | Roflumilast | AVANAFIL besilate |
| 26 | Roflumilast-N-Oxide | AVANAFIL besilate |
| 27 | Roflumilast | BEMINAFIL |
| 28 | Roflumilast-N-Oxide | BEMINAFIL |
| 29 | Roflumilast | BEMINAFIL sodium |
| 30 | Roflumilast-N-Oxide | BEMINAFIL sodium |
| 31 | Roflumilast | BEMINAFIL ethanolamine |
| 32 | Roflumilast-N-Oxide | BEMINAFIL ethanolamine |
| 33 | Roflumilast | DASANTAFIL |
| 34 | Roflumilast-N-Oxide | DASANTAFIL |
| 35 | Roflumilast | UDENAFIL |
| 36 | Roflumilast-N-Oxide | UDENAFIL |
| 37 | Roflumilast | BMS-341400 |
| 38 | Roflumilast-N-Oxide | BMS-341400 |

Pharmacology

Reduction of Pulmonary Arterial Pressure (PAP), Right Ventricular Hypertrophy and Distal Muscularization by the Selective PDE4 Inhibitor Roflumilast in Chronic Pulmonary Hypertension Induced by Hypoxia or Monocrotalin in Rats Objective The objective of the pharmacological investigation was to characterize the effect of orally administered Roflumilast at 0.5 mg kg$^{-1}$ d$^{-1}$ and 1.5 mg kg$^{-1}$ d$^{-1}$ on the increase in mean PAP and RV/LV+S ratio as well as distal arteriolar muscularization triggered by chronic hypoxia or monocrotalin (MCT) in rats. Hypoxia- or MCT-induced pulmonary hypertension in rats represent widely accepted animal models to study the potential of investigative drugs to reverse chronic pulmonary hypertension based on pulmonary vascular remodelling. In the MCT setting Roflumilast was administered both in preventive and curative paradigms.

Animals

Experiments were performed with adult male Wistar rats (200-250 g) according to institutional guidelines abiding to national and international regulations.

Chronic Hypoxic Pulmonary Hypertension

Rats were exposed to chronic hypoxia (10% $O_2$) in a ventilated chamber (500-liter volume, Flufrance, Cachan, France). To establish the hypoxic environment, the chamber was flushed with a mixture of room air and nitrogen, and the gas was recirculated. The environment within the chamber was monitored using an oxygen analyzer (Oxiquant M, EnviTeC—Wismar, Germany). Carbon dioxide was removed by self-indicating soda lime granules. Excess humidity was prevented by cooling of the recirculation circuit. The chamber temperature was maintained at 22-24° C. The chamber was opened every other day for 1 hour to clean the cages and replenish food and water supplies. Normoxic control rats were kept in the same room with identical light-dark cycle. Rats exposed to chronic hypoxia were randomly assigned to three groups (8-10 animals per group): the first group received Roflumilast at 0.5 mg kg$^{-1}$ d$^{-1}$, the second group received Roflumilast at 1.5 mg kg$^{-1}$ d$^{-1}$, the third group received vehicle (methocel). A group not exposed to hypoxia served as control. Roflumilast or vehicle were administered once daily by gavage over 15 days of exposure to hypoxia.

Monocrotaline (MCT)-Induced Pulmonary Hypertension

Rats were randomly assigned to three groups (8-10 animals in each group): two groups received Roflumilast 0.5 and 1.5 mg kg$^{-1}$ d$^{-1}$, respectively; and one group received vehicle. In the preventive treatment paradigm Roflumilast or vehicle were given once daily by gavage for 21 days starting immediately after a single subcutaneous injection of MCT (60 mg kg$^{-1}$). A group not receiving MCT served as control. In a curative approach rats were left untreated for 21 days following MCT (60 mg/kg s.c.) and than randomly divided into two groups, one received roflumilast (1.5 mg/kg/d) p.o. and the other vehicle, from day 21 to day 42.

Assessment of Pulmonary Hypertension

At the end of the treatment period rats were anaethesized with sodium pentobarbital (60 mg/kg, i.p.). A polyvinyl catheter was introduced into the right jugular vein and pushed through the right ventricle into the pulmonary artery. Another polyethylene catheter was inserted into the right carotid artery. After measurement of pulmonary (PAP) and systemic arterial pressures (SAP), the thorax was opened and the left lung immediately removed and frozen in liquid nitrogen. The heart was dissected and weighed for calculation of the right ventricular hypertrophy index (ratio of right ventricular free wall weight over sum of septum plus left ventricular free wall weight; RV/LV+S). The right lung was fixed in the distended state with formalin buffer. After routine processing and paraffin embedding, multiple sections from each lobe were stained with haemotoxylin and eosin. In each rat, 60 intraacinar arteries were analyzed and categorized as muscular (fully or partially) or nonmuscular to assess the degree of muscularization. In addition, intraacinar fully muscularized arteries were evaluated for measurements of medial wall thickness which was calculated and expressed as follows: index (%)= (External diameter−internal diameter)/External diameter× 100%.

Statistical Analyses

The data are expressed as means±SEM. A nonparametric Mann-Whitney test was used for comparisons between two groups. Comparisons of data at various times after MCT injection or of various treatment groups were performed using a nonparametric Kruskal-Wallis test followed by Dunn's test when significant. To compare the degree of pulmonary vessels muscularization between groups, we used a non parametric Mann-Whitney or a Kruskal-Wallis test after ordinal classification of the vessels as non muscular, partially muscular, or fully muscular.

Results

Effects of Roflumilast on the Development of Chronic Hypoxic Pulmonary Hypertension Rats exposed over 15 days to chronic hypoxia developed pulmonary hypertension associated with right ventricular hypertrophy reflected by an increase in mean pulmonary artery pressure (mean PAP) and RV/LV+S ratio. The selective PDE4 inhibitor Roflumilast reduced mean PAP augmented by chronic hypoxia at both 0.5 mg kg$^{-1}$ d$^{-1}$ and 1.5 mg kg$^{-1}$ d$^{-1}$ (p<0.05 vs vehicle) in a dose dependent manner (Table 3). Systemic arterial pressure and heart rate remained unaffected by the treatment regimen. In parallel, the increase of RV/LV+S ratio following persistent hypoxia was partially reversed by Roflumilast, to a higher extent at 1.5 mg kg$^{-1}$ d$^{-1}$ (p<0.01 vs vehicle) compared to 0.5 mg kg$^{-1}$ d$^{-1}$ (Table 3).

Increased muscularization of distal pulmonary arterioles may cause PAP increase and right ventricular hypertrophy. Roflumilast significantly (p<0.001) reduced distal muscularization augmented by chronic hypoxia over 15 days with higher efficacy at 1.5 mg kg$^{-1}$ d$^{-1}$ compared to 0.5 mg kg$^{-1}$ d$^{-1}$ (Table 3).

TABLE 3

Effects of roflumilast on pulmonary arterial haemodynamics and muscularization of distal pulmonary arteries in chronic hypoxia-induced pulmonary arterial hypertension in rats

| | PAP [mm Hg] | RV/LV + S [%] | Muscularization [%] |
|---|---|---|---|
| Control | 17 ± 1 | 26 ± 1.1 | 9 ± 3 |
| Hypoxia | 30.8 ± 2.4 | 42.6 ± 1.6 | 57 ± 3 |
| Hypoxia + 0.5 mg/kg Roflumilast | 28 ± 1.8 | 37.8 ± 2.3 | 31.8 ± 2 |
| Hypoxia + 1.5 mg/kg Roflumilast | 25.5 ± 1.8 | 30.5 ± 0.8 | 18.5 ± 2 |

Effects of Roflumilast on the Development of MCT-Induced Pulmonary Hypertension

Monocrotaline produced severe pulmonary hypertension in rats characterized by a substantial increase in mean PAP, RV/LV+S, and muscularization of distal pulmonary arterioles after 21 days. Roflumilast reduced mean PAP and right ventricular hypertrophy with higher potency at 1.5 mg kg$^{-1}$ d$^{-1}$ (p<0.01 vs vehicle) versus 0.5 mg kg$^{-1}$ d$^{-1}$ (p<0.05 vs vehicle) (Table 4). The improvement of these haemodynamic parameters of pulmonary circulation was complemented by a dose-dependent, significant (p<0.001) decrease in muscularization of distal pulmonary arterioles caused by the selective PDE4 inhibitor (Table 4).

TABLE 4

Effects of Roflumilast on pulmonary arterial haemodynamics and muscularization of distal pulmonary arteries in monocrotaline (MCT)-induced pulmonary arterial hypertension in rats

| | PAP [mm Hg] | RV/LV + S [%] | Muscularization [%] |
|---|---|---|---|
| Control | 14.8 ± 4 | 25 ± 1.4 | 9 ± 3 |
| MCT | 37.6 ± 1.5 | 44.3 ± 1.7 | 77.9 ± 4.8 |
| MCT + 0.5 mg/kg Roflumilast | 29.3 ± 1.3 | 38.9 ± 1.6 | 62.7 ± 5.4 |
| MCT + 1.5 mg/kg Roflumilast | 21.4 ± 2.0 | 31.3 ± 1.8 | 30.3 ± 8.2 |

In a curative approach Roflumilast (1.5 mg/kg/d) p.o. or vehicle were administered beginning at day 21 following MCT i.e. when pulmonary vascular remodeling and consequently augmented PAP and right ventricular hypertrophy were manifest. After another 3 weeks (i.e. at day 42) PAP was measured and rats were sacrificed to assess RV/LV+S ratio and muscularization of distal pulmonary arteries.

TABLE 5

Effects of Roflumilast (1.5 mg/kg/d) p.o. starting day 21 on pulmonary artery haemodynamics and muscularization of distal pulmonary areries in monocrotaline (MCT)-induced pulmonary arterial hypertension in rats (curative approach)

| | PAP [mmHg] | RV/LV + S [%] | Muscularization [%] |
|---|---|---|---|
| Day 0 | 15.1 ± 1.1 | 25.9 ± 1.4 | 9 ± 3 |
| Day 21 | 32.1 ± 0.9 | 46.2 ± 0.9 | 68.2 ± 1.6 |
| Day 42 Vehicle | 37.9 ± 2.8 | 49.2 ± 2.0 | 67.3 ± 2.4 |
| Day 42 Roflumilast | 23.6 ± 0.7 | 33.8 ± 0.9 | 36.4 ± 2.4 |

As expected pulmonary arterial pressure (PAP) and right ventricular hypertrophy (RV/LV+S) ratio further increased from day 21 to day 42 in the vehicle group. However, treatment with Roflumilast from day 21 reduced PAP and RV/LV+S ratio at day 42 even beyond the values at day 21. These haemodynamic findings may have been caused by a distinct reduction of muscularization of the distal pulmonary arteries with Roflumilast. More specifically, ~70% of these arterioles were fully muscularized at day 21 as well as on day 42 of the vehicle group. Roflumilast from day 21 significantly reduced the proportion of fully muscularized arterioles by >50% at day 42. Medial wall thickness index of the fully muscularized pulmonary arterioles [calculated as (external diameter−internal diameter)/external diameter×100%] that increased to 51±3% at day 21 after MCT persisting at 52±4% at day 42 in the vehicle group was significantly reduced by Roflumilast (from day 21) to 18±2% at day 42. Importantly, the ratio of completely obliterated arterioles at day 42 was significantly lower in rats that received Roflumilast from day 21 (30±5%) compared to day 21 (50±1%) or day 42 in the vehicle group (66±3%). Proliferating Cell Nuclear Antigen (PCNA) labeling of smooth muscle cells in the walls of distal pulmonary arteries was present following MCT however, abolished in the Roflumilast (1.5 mg/kg/d) groups indicating that the PDE4 inhibitor effectively inhibited proliferation of pulmonary artery smooth muscle cells in vivo. In the curative approach the survival rate was significantly improved by Roflumilast (1.5 mg/kg/d). Whereas 21 of 39 (54%) of the rats in the vehicle group survived up to day 42, from the 24 rats in the Roflumilast group 17 (71%) animals were alive at day 42. Taken together in the paradigm of MCT-induced pulmonary vascular remodeling and consecutive pulmonary arterial hypertension in rats administration of Roflumilast (1.5 mg/kg/d) following the curative protocol operated a partial regression of pre-existing pulmonary vascular remodeling and hence, pulmonary arterial hypertension.

CONCLUSION

Roflumilast dose-dependently improved chronic pulmonary hypertension triggered by hypoxia or monocrotaline in rats, while systemic arterial pressure and heart rate remained unaffected.

The invention claimed is:

1. A method for the reduction of pulmonary vascular remodeling in a patient suffering from pulmonary hypertension comprising administering to said patient in need thereof an effective amount of an active compound selected from the group consisting of Roflumilast, a pharmaceutically acceptable salt of Roflumilast, Roflumilast-N-Oxide and a pharmaceutically acceptable salt of Roflumilast-N-Oxide, wherein said active compound is the sole active compound administered to said patient.

2. The method according to claim 1, wherein the active compound is selected from the group consisting of Roflumilast and a pharmaceutically acceptable salt of Roflumilast.

3. The method according to claim 1, wherein the active compound is selected from the group consisting of Roflumilast-N-Oxide and a pharmaceutically acceptable salt of Roflumilast-N-Oxide.

4. The method according to claim 1, wherein the active compound is Roflumilast.

5. The method according to claim 1, wherein the active compound is Roflumilast-N-Oxide.

* * * * *